United States Patent
Amirkhanian et al.

(10) Patent No.: US 8,784,626 B2
(45) Date of Patent: Jul. 22, 2014

(54) BIO-ANALYSIS USING BALL-ENDED INCIDENT AND OUTPUT OPTICAL FIBERS

(75) Inventors: Varouj D. Amirkhanian, La Crescenta, CA (US); Shou-Kuan Tsai, New Taipei (TW)

(73) Assignee: Bioptic, Inc., New Taipei (TW)

( * ) Notice: Subject to any disclaimer, the term of this patent is extended or adjusted under 35 U.S.C. 154(b) by 328 days.

(21) Appl. No.: 13/016,944

(22) Filed: Jan. 28, 2011

(65) Prior Publication Data
US 2011/0253540 A1 Oct. 20, 2011

Related U.S. Application Data

(60) Provisional application No. 61/299,301, filed on Jan. 28, 2010.

(51) Int. Cl.
*B03C 5/02* (2006.01)
*G01N 27/447* (2006.01)

(52) U.S. Cl.
CPC .... *G01N 27/44721* (2013.01); *G01N 27/44756* (2013.01)
USPC ........... 204/451; 204/601; 204/452; 204/453; 204/454; 204/455

(58) Field of Classification Search
USPC .................. 204/451–455, 601–605; 356/344, 356/432–444
See application file for complete search history.

(56) References Cited

U.S. PATENT DOCUMENTS

| 4,675,300 | A | * | 6/1987 | Zare et al. | 204/452 |
| 4,985,129 | A | * | 1/1991 | Burd | 204/603 |
| 5,963,456 | A | * | 10/1999 | Klein et al. | 702/19 |
| 2001/0040094 | A1 | * | 11/2001 | Inaba et al. | 204/603 |
| 2002/0092770 | A1 | * | 7/2002 | Hedberg et al. | 204/603 |
| 2003/0116436 | A1 | * | 6/2003 | Amirkhanian et al. | 204/452 |
| 2004/0115648 | A1 | * | 6/2004 | Mooney et al. | 435/6 |
| 2004/0246597 | A1 | | 12/2004 | Ono et al. | |

FOREIGN PATENT DOCUMENTS

| EP | 1338890 | 8/2003 |
| WO | 01/38844 | 5/2001 |
| WO | 2007/002560 | 1/2007 |

OTHER PUBLICATIONS

International Search Report of Counterpart PCT App. No. PCT/US2011/023071.
Schafer, et al., "Microfluidic Cell Counter with Embedded Optical Fibers Fabricated by Femtosecond Laser Ablation & Anodic Bonding", Optics Express, vol. 17, No. 8, Mar. 31, 2009, pp. 6068-6073.
Fleger, et al., "Microfabricated Polymer Analysis Chip for Optical Detection", MICRO tec. 2003, vol. 151, No. 4, Apr. 15, 2004, pp. 159-161.
Camou, et al., "PDMS 2D Optical Lens Integrated with Microfluidic Channels: principle & characterization", Lab on a Chip, Royal Society of Chemistry, Cambridge, GB, vol. 3, No. 1, Feb. 1, 2003, pp. 40-45.
Hsiung, et al., "Microcapillary Electrophoresis Chip Device Integrated with Micro Focusing Lens Structures & Its Biomedical Applications", FOOYIN Journal of Health Sciences, vol. 1, No. 1, Aug. 1, 2009, pp. 11-20.

* cited by examiner

*Primary Examiner* — Bach Dinh
(74) *Attorney, Agent, or Firm* — Liu & Liu

(57) ABSTRACT

A detection optics configuration for bio-analysis, in which the direction of incident radiation, the axis of the separation channel, and the direction of collection of the output radiation are coplanar at the detection zone. The detection configuration incorporates ball-end optical fibers to direct incident radiation at and collection of output radiation from the detection zone. The detection optics configuration may be implemented in an improved bio-separation instrument, in particular a capillary electrophoresis instrument.

17 Claims, 6 Drawing Sheets

US 8,784,626 B2

BIO-ANALYSIS USING BALL-ENDED INCIDENT AND OUTPUT OPTICAL FIBERS

PRIORITY CLAIM

This application claims the priority of U.S. Provisional Patent Application No. 61/299,301 filed on Jan. 28, 2010, which is fully incorporated by reference as if fully set forth herein.

BACKGROUND OF THE INVENTION

1. Field of the Invention

The present invention relates to detection techniques in bio-analysis, particularly detection of bio-separation through a separation channel, and more particularly to optics relating to application of incident radiation at and detection of output radiation from a detection zone along the separation column, e.g., a capillary column. The present invention further relates to a bio-separation instrument incorporating the detection technique, in particular a capillary electrophoresis instrument.

2. Description of Related Art

Currently, most of bio-separation tools applied in the laboratories utilize slab gel based electrophoresis technologies, which have routinely been used for bio-analysis of bio-molecules (i.e. DNA, Protein & Carbohydrate) applications since their inception more than 20 years ago. However, slab gel electrophoresis for bio-analysis is labor intensive and needs to be drastically improved in terms of resolving power, throughput and cost per sample.

Capillary electrophoresis (CE) is a micro fluidic approach to gel-electrophoresis (micro-channel device to simplify gel-electrophoresis), whose greatest advantage is its diverse range of applications. CE technology is commonly accepted by the biotechnology industry specifically in the nucleic acid-based testing as a reliable, high resolution and highly sensitive detection tool, and CE has been applied for protein, carbohydrate and DNA-related analyses such as oligonucleotides analysis, DNA sequencing, and dsDNA fragments analysis. CE is commonly avoided in routine analysis because it is reputed to be a troublesome technique with high failure rates. However this is no longer true because instrument manufacturers have drastically improved instrument design and overall CE knowledge has increased. There are three key factors for reducing failure rate and producing accurate, precise and robust CE data: operator training, system stability, and operation ease of the instrument with low maintenance.

Capillary Electrophoresis Immunoassay Analysis (CEIA) has recently emerged as a new analytical technique, when combined with sensitive detection methods such as Laser Induced Fluorescence (LIF), offers several advantages over the conventional immunoassays. CEIA can perform rapid separations with high mass sensitivity, simultaneously determine multiple analytes and is compatible with automation. Use of CE and florescence labeled peptides can be used to detect abnormal prion protein in the blood of animals. One such CE-based noncompetitive immunoassay for Prion Protein using Fluorescein isithiocyanate (FITC)-labeled Protein A as Fluorescent probe method has successfully been applied for testing blood samples from scrapie-infected sheep.

Further, immunoassays are commonly used in biotechnology for the detection and quantification of host cell contaminants. The free-solution approach by CE with fluorescence type detection has brought an exciting alternative to solid-phase immunoassay. The CE with fluorescent type detection eliminates antigen immobilization and avoids many solid-phase-associated problems. This methodology makes use of either a purified antigen labeled with stable fluorescent dye (i.e. FITC) or an affinity probe labeled with the dye (direct assay).

Without a doubt, CE with laser-induced fluorescence (LIF) is one of the most powerful analytical tools for rapid, high sensitivity and high-resolution dsDNA analysis and immunoassay analysis applications. However, the current selling price for CE-based LIF systems is much more expensive than traditional slab-gel based bio-analysis systems due to the complicated optical detection mechanism. The expensive CE-based systems are thus out of reach for all but a few well-funded laboratories and seems to be a high-cost barrier for the expansion of immunoassay type analysis applications/business.

There is a need for a system with a less complex optical detection mechanism to reduce costs, which complements simplicity in operation, rapid analysis with high efficiency, sensitivity and throughput.

SUMMARY OF THE INVENTION

The present invention provides a simplified, low cost, efficient, highly sensitive, non-moving and stable micro-optical detection configuration for bio-separation (e.g., capillary electrophoresis) through a separation channel (e.g., defined by a column) filled with a separation support medium (e.g., a liquid or sieving gel including a running buffer). More particularly, the present invention is directed to an improved detection configuration that includes optics for application of incident radiation at and detection of output radiation from a detection zone along the separation channel, for the detection of radiation emitted by sample analytes (e.g., radiation induced fluorescence emission).

In one aspect of the present invention, the direction of incident radiation (e.g., from a laser or LED source), the axis of the separation channel at the detection zone, and the direction of collection of the output radiation are all substantially in the same plane. In one embodiment, the incident radiation is provided to the detection zone and/or the output radiation is collected from the detection zone, using light guides in the form of optical fibers. In an embodiment, the detection configuration of the present invention has optical fibers positioned at opposite sides of the detection zone along the separation channel. The optical fibers may be positioned at less than 180 degrees (e.g., 40 to 160 degrees, such as 120 degrees) apart from each other for high detection sensitivity.

In another aspect of the present invention, the detection configuration of the present invention incorporates ball-end optical fibers to provide incident radiation and collection of output radiation.

In a further aspect of the present invention, the detection optics configuration of the present invention may be implemented in an improved bio-separation instrument, in particular a capillary electrophoresis instrument.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides a simplified, low cost, efficient, highly sensitive, non-moving and stable micro-optical detection configuration for bio-separation (e.g., capillary electrophoresis) through a separation channel (e.g., defined by a column) filled with a separation support medium (e.g., a liquid or sieving gel including a running buffer). More particularly, the present invention is directed to an improved detection configuration that includes optics for application of incident radiation at and detection of output radiation from a detection zone along the separation channel, for the detection of radiation emitted by sample analytes (e.g., radiation induced fluorescence emission). In one aspect of the present invention, the direction of incident radiation (e.g., from a laser or LED source), the axis of the separation channel at the detection zone, and the direction of collection of the output radiation are all substantially in the same plane. In another aspect of the present invention, the detection configuration of the present invention incorporates ball-end optical fibers to provide incident radiation and collection of output radiation. The present invention further relates to an improved bio-separation instrument incorporating the detection configuration of the present invention.

For purpose of illustrating the principles of the present invention and not limitation, the present invention is described by reference to embodiments directed to capillary electrophoresis using a capillary separation column. Further, the present invention will be described, without limitation, in connection with radiation induced fluorescence detection (e.g., using a laser or LED source). Fluorescence is a spectrophotometric method of analysis where the molecules of the analytes are excited by irradiation at a certain wavelength and emit radiation at a different wavelength. The emission spectrum provides information for both qualitative and quantitative analysis. Generally, the advantage of fluorescence detection over absorbance detection is the superior detectability (detection sensitivity). For efficient fluorophores, single molecule detection in small volumes has been demonstrated. This is in part because fluorescence signal is measured against a relatively dark background, as a result of the emitted radiation being detected at a wavelength that is different from the wavelength of the incident radiation (e.g., the wavelength of the emitted fluorescence is at longer wavelengths than the excitation radiation).

Figure 1:
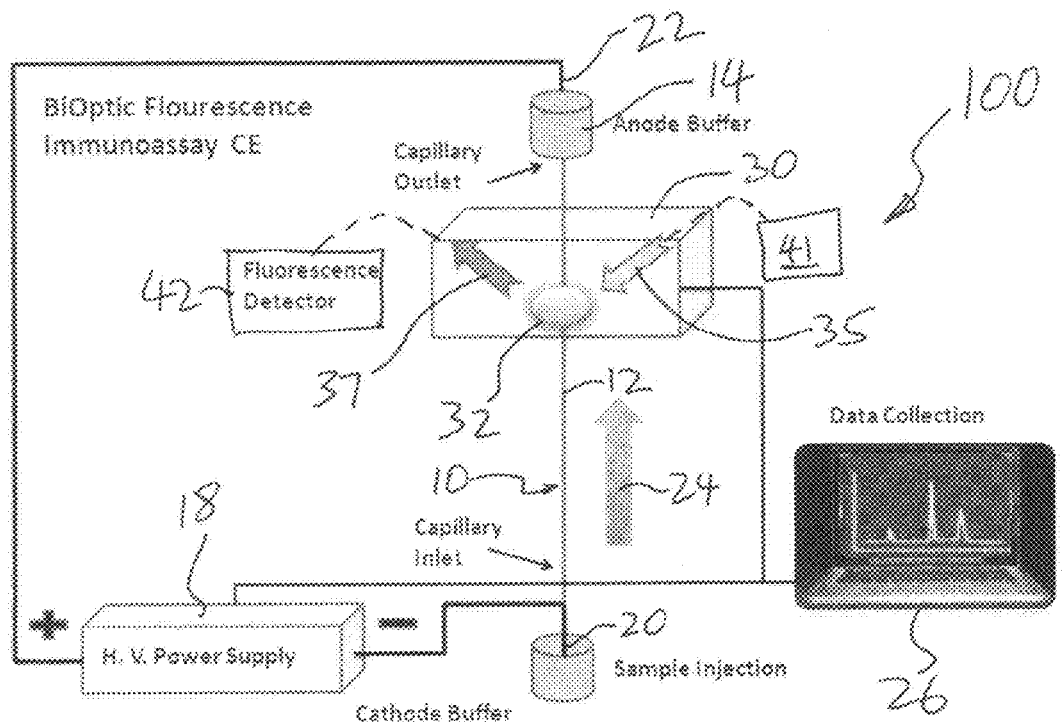
FIG. 1 is a schematic view of a capillary electrophoresis system that incorporates the optical detection configuration in accordance with one embodiment of the present invention.

Referring to FIG. 1, a capillary electrophoresis (CE) system 100 that incorporates the novel detection configuration of the present invention is schematically illustrated. The CE system 100 generally comprises a capillary separation column 10 (e.g., 200-500 µm O.D.), which defines an internal separation channel 12 (e.g., 25-150 µm I.D.). The capillary column 10 may be made of fused silica, glass, polyimide, or other ceramic/glassy materials. The inside walls of the separation column 10 (i.e., the walls defining the separation channel 12) may be coated with a material that can build up an electrostatic charge to facilitate electrophoresis and/or electrokinetic migration of the sample components. The separation channel 12 may be filled with a separation support medium, which may be simply a running buffer, or a sieving gel matrix (of a linear or non-linear polymeric composition) known in the art.

One end of the capillary column 10 is coupled to a reservoir 14 of running buffer. The other end of the capillary column 10 is coupled to another reservoir 16, which may alternately contain a sample (to be injected into the separation channel 12) and running buffer (after sample injection, to undertake separation). A power supply 18 supplies a high voltage to the reservoirs 14 and 16 via electrodes 20 and 22.

The mechanism of electrophoresis and radiation induced fluorescence when considered alone are outside the scope of the present invention. For the sake of completeness, it is sufficient to briefly mention the operation of the CE system 100. In operation, a prepared biological sample, tagged with a known fluorophore, is introduced into the far end of the capillary column away from the detection zone, by any of a number of ways that is not part of the present invention (e.g., electrokinetic injection from a sample reservoir or physical pressure injection using a syringe pump). When a DC potential (e.g., 1-30 KV) is applied by the power supply 18 to the electrodes 20 and 22, the sample migrates under the applied electric potential along the separation channel 12 in the direction 24 (e.g., sample that is negatively charged travels toward the positive electrode 22 as shown in FIG. 1) and separates into bands of sample components. The extent of separation and distance moved along the separation channel 12 depends on a number of factors, such as migration mobility of the sample components, the mass and size or length of the sample components, and the separation support medium. The driving forces in the separation channel 12 for the separation of samples could be electrophoretic, pressure, or electro-osmotic flow (EOF) means.

When the sample reaches the detection zone 32, excitation radiation is directed via the excitation fiber 34 in a direction 35 at the detection zone 32. The sample components would fluoresce with intensities proportional to the concentrations of the respective sample components (proportional to the amount of fluorescent tag material). The detector 42 detects the intensities of the emitted fluorescence via the emission fiber 36 in a direction 37, at a wavelength different from that of the incident radiation. The detected emitted radiation may be analyzed by known methods. For an automated system, a controller 26 (e.g., in the form of a notebook computer or a desktop computer) having a processor, controls the operations of the various components in the CE system 100 to effect capillary electrophoresis separation and data collection. Such control is well the knowledge of one skilled in the art.

Figure 2:
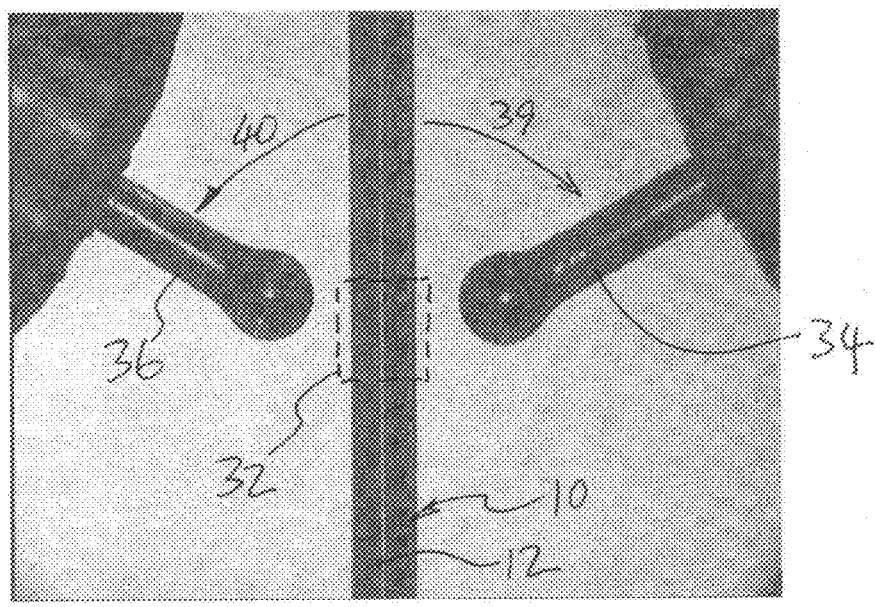
FIG. 2 illustrates the detection region, showing the configuration of the excitation fiber, emission fiber and the capillary column.

In the particular illustrated embodiment in FIG. 1, the detection optics configuration (schematically indicated in the area 30 located about a detection window/zone 32) corresponds to the embodiment illustrated in FIG. 2. The direction 35 of incident radiation (e.g., from a laser or LED source), the axis of the separation channel at the detection zone, and the direction 37 of collection of the output radiation are all substantially in the same plane. In the illustrated embodiment, the detection configuration of the present invention has optical fibers positioned at opposite sides of the detection zone separation channel. In one embodiment, the incident radiation is provided to the detection zone and/or the output radiation is collected from the detection zone, using light guides in the form of optical fibers, in particular ball-ended optical fibers (i.e., optical fibers terminating in a micro ball that is integral to the fiber end in a unitary structure).

Referring also to FIG. 2, a ball-ended fiber (the excitation fiber 34) extends from a radiation source (e.g., LED or laser source 41, schematically shown in FIG. 1) to direct excitation radiation in a direction 35 at the detection zone 32. The ball end of the excitation fiber 34 is positioned at or proximate to the exterior surface of the separation column 10 about the detection zone 32. In the illustrated embodiment, the ball end of the excitation fiber 34 is positioned at a distance spaced from the exterior surface of the separation column 10 (i.e., non-contact mode). In this illustrated embodiment, another ball-ended fiber (the emission fiber 36) extends to a detector (e.g., a fluorescence detector 42, schematically shown in FIG. 1) to collect emitted radiation at a direction 37 from the detection zone 32. The ball end of the emission fiber 36 is positioned at or approximate to the exterior surface of the separation column 10 about the detection zone 32. In the illustrated embodiment, the ball end of the emission fiber 36 is positioned at a distance spaced (in a non-contact mode) from the exterior surface of the separation column 10. Both excitation and emission fibers 34 and 36 with ball tips are positioned at opposite sides of the separation column 10 in a non-contact mode (spaced from the exterior of the capillary column) to reduce background fluorescence and not cause any physical damage to either capillary column or the microball.

In the illustrated embodiment in FIG. 2, the components at the detection zone 32 as shown in FIG. 2 lie in substantially the same plane. Specifically, the longitudinal axis of the excitation fiber 34, the longitudinal axis of the emission fiber 36 and the longitudinal axis of the capillary channel 12, are substantially aligned in the same plane (i.e., substantially coplanar), at least at the region of the detection zone 32. That is, while the lengths of the excitation fiber 34, the emission fiber 36 and the capillary column 10 may be bent overall, however at least near the detection zone region, the axis of the excitation fiber 34, the axis of the emission fiber 36 and the axis of the capillary channel 12 are substantially aligned in the same plane, such that the direction 35 of incident radiation from the excitation fiber 34 towards the detection zone 32, the axis of the separation channel 12 at the detection zone 32, and the direction 37 of collection of the output radiation away from the detection zone along the emission fiber 36 are all substantially in the same plane.

Further, at the detection zone 32, the angle between the axis of the excitation fiber 34 and the axis of the emission fiber 36 are not aligned in a straight line. At least one of the axis of the excitation fiber 34 and the axis of the emission fiber 36 is not perpendicular to the axis of the separation channel 12 at the detection zone 32. In the illustrated embodiment shown in FIG. 2, both the axis of the excitation fiber 34 and the axis of the emission fiber 36 are not perpendicular to the axis of the separation channel, and are at angles 39 and 40, respectively, to the axis of the separation channel 12 at the detection zone 32. The angle 39 and the angle 40 may be substantially the same or different, and may be less than or greater than 90 degrees measured with respect to a reference direction of the axis of the separation channel 12 or a reference section of the capillary column 10 (e.g., the section of capillary column 10 between the fibers 34 and 36 as shown in FIG. 2). For example, the angle 39 may be less than 90 degrees and the angle 40 may be greater than 90 degrees, measured from the same reference section. In the illustrated embodiment in FIG. 2, the angles 39 and 40 are same and substantially in the same plane.

In the embodiment illustrated in FIG. 2, both the excitation fiber 34 and the emission fiber 36 each has a 200 micron diameter core as light guide within an external cladding, and a 350 micron diameter ball shaped tip (i.e., the ratio of the fiber core diameter to the ball diameter is 1:1.75), which comprises fused the core and cladding material. The ball shaped tip has a substantially spherical profile. The ball-end fibers may be formed by using a fusion splicer, or are available from a number of available suppliers. The capillary column 10 has an outside diameter of 200 to 370 micron (e.g., 360 micron) and an internal diameter of 20 to 150 micron (e.g., 75 micron). The tip of the ball end of the excitation fiber 34 is spaced at approximately 50-500 micron from the external surface of the capillary column, and the tip of the ball end of the emission fiber 36 is spaced at approximately 10 to 500 microns (e.g., 50-200 micron) from the external surface of the capillary column. Alternatively, the emission fiber 36 may have a 300 micron diameter core with a 500 micron diameter ball shaped tip at its distal end (i.e., the ratio of the fiber core diameter to the ball diameter is 1:2.5). The angles 39 and 40 each may range from greater than 0 to less than 90 degrees, preferably between 20 to 70 degrees, and more preferably at 30 to 45 degrees. In the illustrated embodiment of FIG. 2, both angles 39 and 40 are about 70 degrees.

In one embodiment, the optical detection system is structured with a super-bright royal blue LED (e.g., Cree XLamp) as excitation radiation source for the fluorescent labeled (FITC) antibody fragment detection. The modular design and fiber optic coupling provides flexibility for exchanging the excitation radiation to a laser module (for LIF applications) or other type of inexpensive light sources.

It has been found that compared with flat-end fibers (bare fiber, with no micro ball lens, the ball-ended fibers (FIG. 4) provide good focusing of incident radiation (light concentration/power density) for the excitation fiber 34 and high collection efficiency (high Numerical Aperture NA) for the emission fiber 36 as a high angle fluorescence collector for increased fluorescence signal collection capability and improved detection sensitivity. Using large core (100-1000 micron) and high NA multi-mode fibers, it allows high power light coupling from LED or laser into the excitation fiber 34. By producing an integrated micro ball lens at the distal output end of the excitation fiber 34, it allows good coupling efficiency inside the separation channel 12 (20-200 micron micro-fluidic channel) for high fluorescence detection sensitivity.

Figure 3:
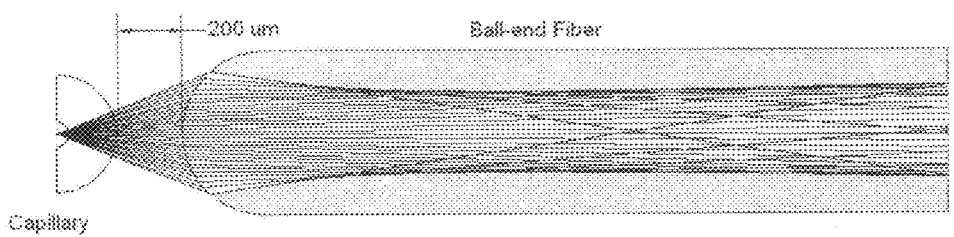
FIG. 3 is a computer simulation of the rays in optical fiber.

A smaller diameter excitation fiber 34 having 200 micron core diameter with a 330-350 micron diameter ball (see FIG. 2) directed at the capillary separation channel 12 results in a smaller focal spot with higher power density, thereby optimizing the fluorescence excitation signal. If an emission fiber 36 having a 300 micron core diameter and a 500 micron diameter ball lens is used for emission collection, the emission collection efficiency is increased. FIG. 3 illustrates the computer simulation of geometrical ray fans from a 300 micron diameter core fiber having a 500 micron ball-end into a silica capillary column. The outside diameter of the capillary column is 360 micron, and the inside diameter is 75 micron.

Comparing to detection configurations disclosed in earlier patents (e.g., U.S. Pat. Nos. 6,184,990; 6,828,567 and 6,870,165), in which the excitation fiber and the emission detection optical axis at 90 degrees out of plane, the present novel approach positions the excitation fiber, emission fiber and the separation channel in substantially the same plane. This configuration provides simplicity in mechanical alignment of the micro-optics with respect to the fluidic channel (glass capillary).

The excitation and emission fibers could be pre-positioned fixed within the body/assembly of a capillary cartridge (may include a separation support medium such as a gel). The 2-fiber detection configuration with ball-end fibers has been applied to a disposable single-channel, single capillary cartridge concept with an integrated buffer reservoir.

Figure 4A:
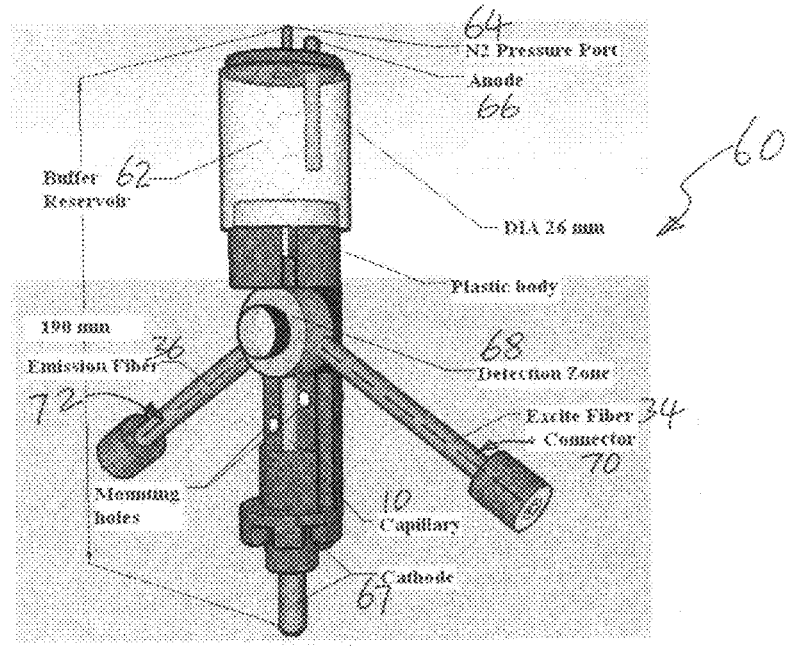
FIG. 4A is a schematic illustration of a capillary cartridge incorporating the detection optic configuration in accordance with one embodiment of the present invention.

FIG. 4A illustrates a single-channel cartridge 60, which is integrated with a top/outlet buffer reservoir 62, which is directly coupled to an external modular air pressure pump (not shown) via pressure port 64. The pressure pump (or a gas tank) provides the required air pressure to fill-up the capillary separation channel 12 in the capillary column 10 with the separation buffer contained in the reservoir 62. Depending on the viscosity of the separation buffer, pressures of up to 60 PSI can be applied to fill the capillary column 10 through the top buffer reservoir 62. The reservoir 62 is provided with a built-in electrode 66 (anode). The lower end of the cartridge 60 is provided with another electrode 67 (cathode). The electrodes 66 and 67 are automatically connected to an external high voltage power supply (not shown) for electrophoresis when installed inside a CE instrument designed to receive the cartridge 60.

Figure 4B:
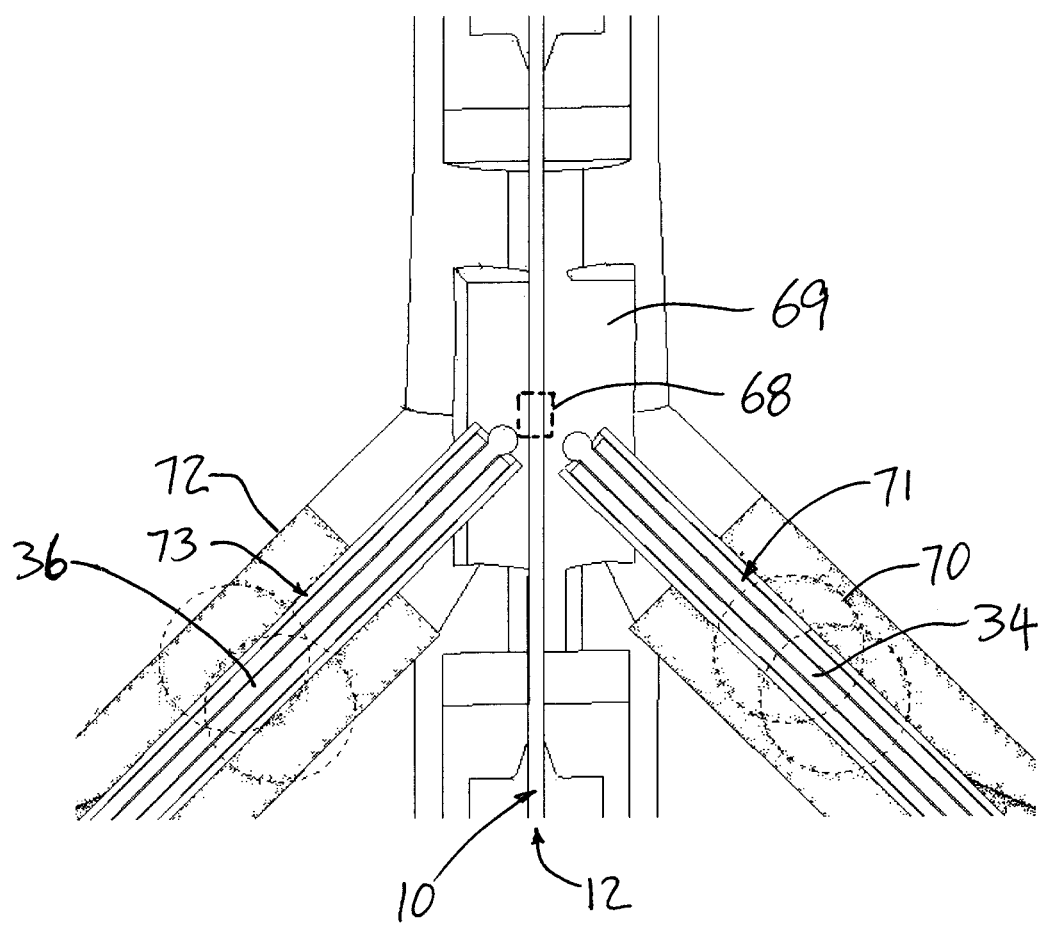
FIG. 4B is a center plane sectional view at the detection region in the capillary cartridge in FIG. 4A.

Referring also to sectional view of FIG. 4B, the internal of the cartridge 60 having a cavity 69 surrounding the region of detection zone 68 is shown. The excitation fiber 34 and emission fiber 36 are supported to align with the detection zone defined in the separation channel/column 10. The axes of the fibers 34 and 36 and the capillary column are coplanar. In the illustrated embodiment, the excitation fiber 34 and emission fiber 36 are supported and aligned within axial channels 71 and 73 (which may also include cylindrical sleeves to hold the fibers) in the cylindrical connectors 70 and 72, which protects the flexible fibers 34 and 36. The ball ends of the fibers 34 and 36 are not touching the capillary column 10.

The test samples are introduced to the separation capillary column 10 by electro kinetic injection. The high voltage power supply (e.g., EMCO, Sutter Creek, Calif.) is used to deliver 500V to 20 KV of electrical field to the capillary for the electro kinetic injection and separations of bio-molecules. An excitation LED having broad band light energy (FWHM=50 nm) and 100 degrees of viewing angle is coupled to the large core excitation fiber (100-1000 micron) at the flat end (polished or cleaved end). A line filter (FWHM=2-50 nm Band Pass line filter) in placed in front of the LED before coupling the light into the 200 micron diameter core with 350 diameter micron ball-ended excitation fiber to reduce background noise. The micro-ball lens end of the fiber is produced by fusion splicing (high voltage heat melting) with a well controlled ball diameter to create a well defined exit NA and spot size for coupling the excitation radiation energy into the inner diameter (the separation channel) of the capillary column (see, FIG. 3 for simulation of a larger core fiber; the simulation is for an emission fiber, but the simulation also applies to a excitation fiber). The fluorescence emission signal produced by the separated analytes are then collected at the detection zone of the capillary channel using a similar ball-ended fiber (larger core fiber with 500 micron diameter ball) and is relayed to an external detector module (not shown, which may be using PMT or SiPMT or CCD) with a build in emission filter (Band Pass Filter=520 nm) for FITC dye related applications (see, results shown in FIG. 5-8).

Figure 5:
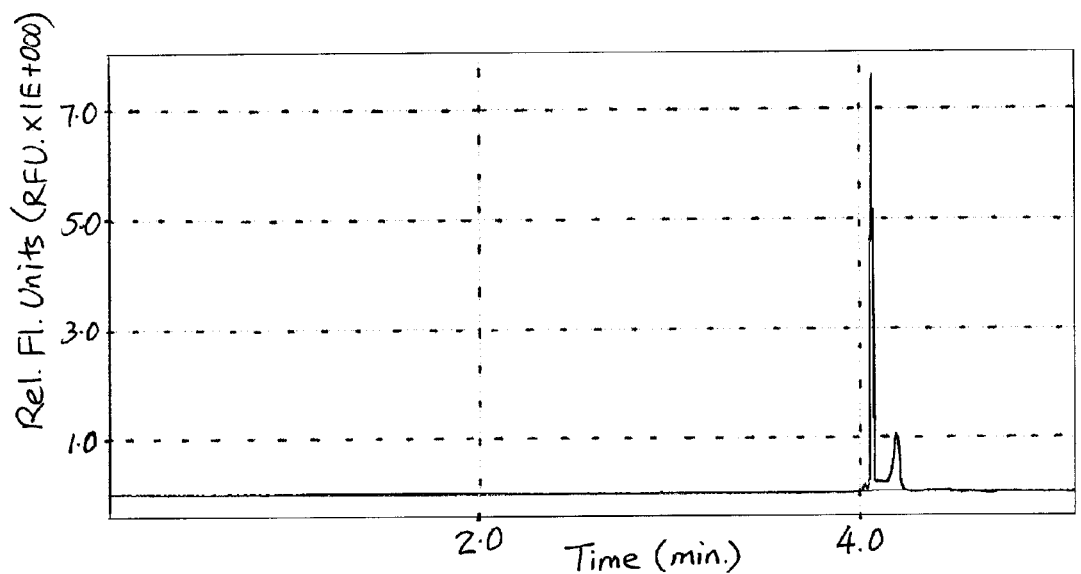
FIGS. 5-8 illustrates results of optical detection.
Figure 6:
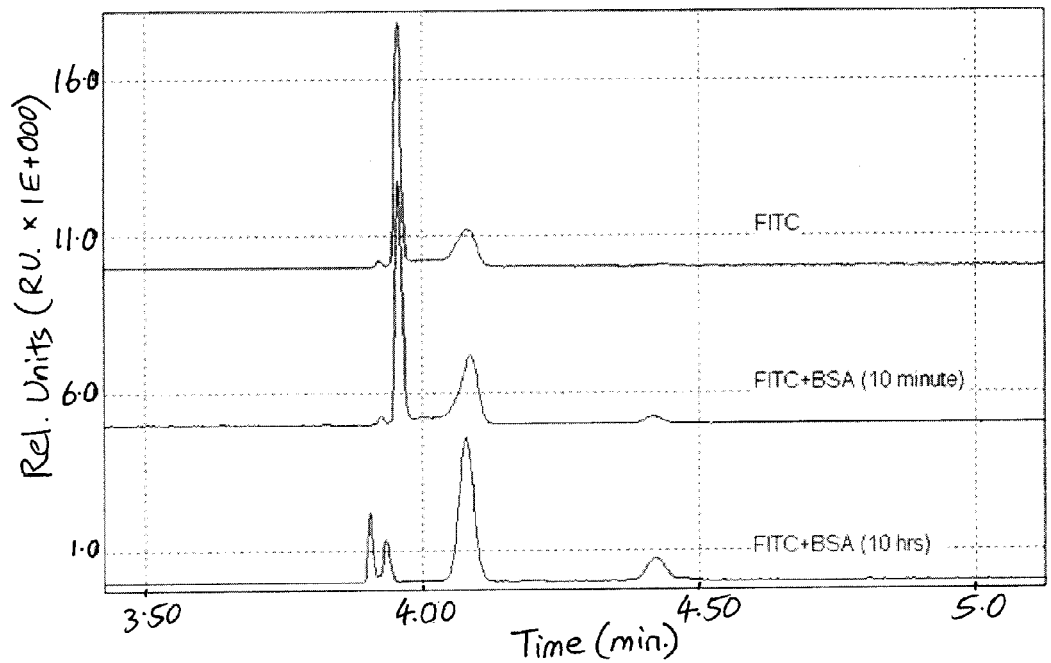
Figure 7:
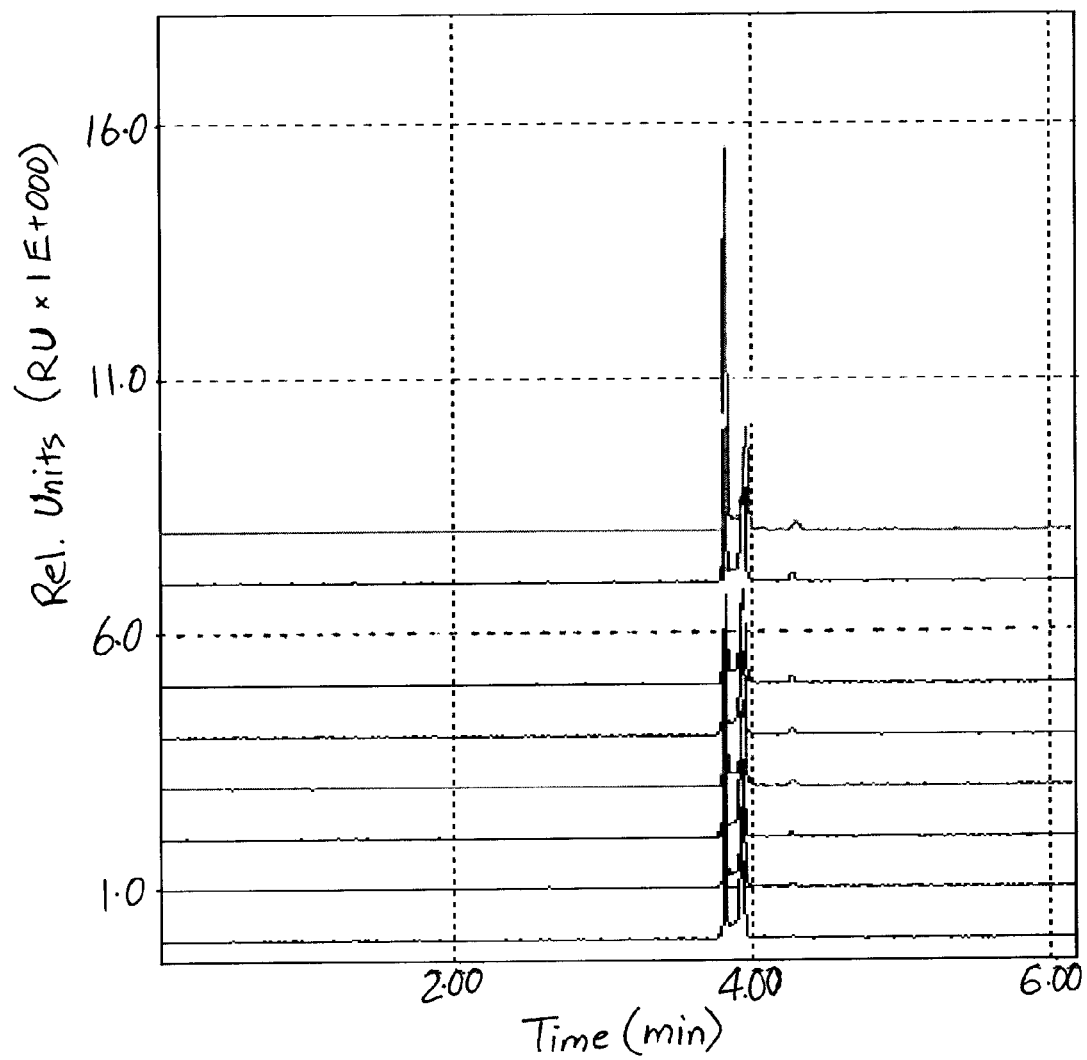
Figure 8:
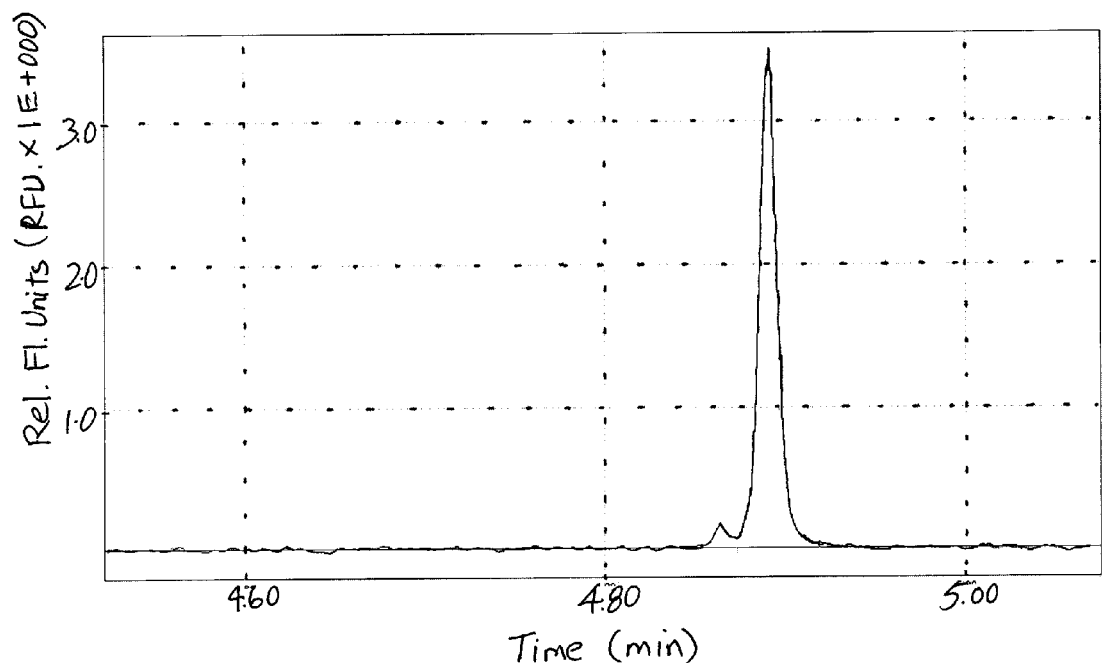

Ball-ended fibers provide a very robust design for large volume manufacturing of detectors for CE systems and provides significant background noise reduction, which results in improved S/N with high detection sensitivity in analysis of bio-molecules (e.g., protein, DNA, carbohydrate or immunoassays type analysis) FIGS. 5-8 illustrate detection results using the novel detection configuration of the present invention. FIG. 5 illustrates Fluorescein Isithiocyanate (FITC concentration at $2\times10^{-5}$M) separated and detected within 4-minutes with baseline Noise (p-p)=0.028 RFU and Signal=7.5 RFU resulting in S/N=268. This test establishes the baseline for the detector performance before running the actual test samples. FIG. 6 illustrates separation and detection of the FITC and FITC conjugated with Bovine serum albumin (BSA) at different times (10 min and 10 hrs). FIG. 7 illustrates reproducibility results (injection of peaks and migration times) for the FITC test marker. FIG. 8 illustrates Anti-Human IgA conjugated to Sigma Fluorescein Isothiocyanate (FITC) diluted to 10% of the stock solution analyzed with the new CE fluorescent detection system (separation is within 4.5 minutes with baseline Noise (p-p)=0.044 RFU and Signal=3.4 RFU providing an S/N=80).

While capillary cartridge with pre-attached fibers provides accurate/fixed coupling with high detection sensitivity, the associated costs are higher, especially for a disposable cartridge. Alternatively, the excitation and emission fibers may be externally brought within close proximity of the detection zone/window of the capillary column by automatic mechanical actuation (e,g, manual latching, pneumatic latching, piezo-actuation or solenoid type actuation). That is, the capillary cartridge does not need to be provided with any detection optics, and external detection optics are coupled to the capillary cartridge when it is installed into a bio-separation instrument. This latter approach provides simplicity in the capillary cartridge mechanical design. With this approach, capillary cartridge disposable assembly do not need to include pre-assembled excitation and emission fibers within the assembly/package, but facilitate automated actuation of ball ended fibers to engage the capillary cartridge. This provides ease in assembly and reduced cost for disposable cartridges.

Other embodiments of integral micro-optical couplings at the end of fibers, such as cone-shaped, round or flat ended types, could also be used for light coupling with the separation channel for reduced background light (noise) and increased sensitivity.

Figure 9:
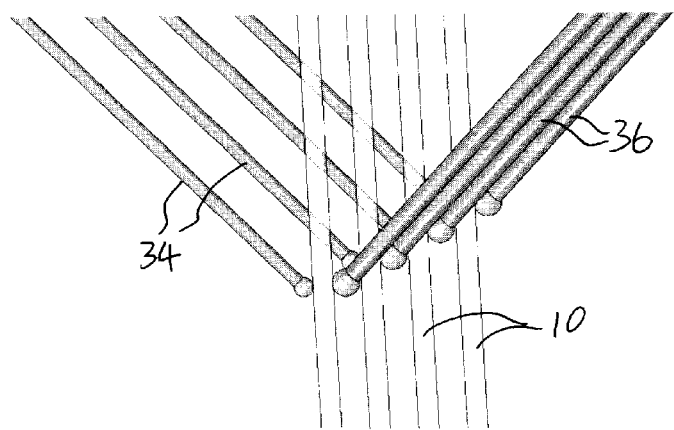
FIG. 9 is a schematic illustration of the detection region for a multi-channel separation system.

The simplicity of the micro-optical detection also provides flexibility in designing higher throughput (i.e. multi-channel, e.g., 12-channel) type gel-cartridge without the use of optics (excitation or emission optics) inside the cartridge assembly 60, which makes the new design lower in cost for a true disposable type cartridge product. FIG. 9 schematically illustrates a multi-channel optical detection configuration incorporating ball-ended excitation fibers 34 and emission fibers 36 aligned with capillary columns 10.

Accordingly, the new fluorescence fiber-based detection for the CE system in accordance with the present invention provides simplicity in design, ease of operation and lower cost consumable. It provides a good solution particularly for the research and clinical diagnostic laboratories/industry that demands sustained and stable recurring revenue streams from both an installed base of instruments and recurring need for consumables such as testing reagents and buffer containing capillary cartridge (classical razor/razor blade business model).

The simplicity of this design allows one to incorporate the fibers in a mechanical actuator for use with multi-channel, multi-capillary electrophoresis system, which obviates the need to include structures for pre-assembling the fiber or other micro-optics within the multi-channel capillary cartridge design. The flexibility in the optical detection design allows simplicity in cartridge design for 12-capillaries at much reduced cost than the capillary cartridge and detection system disclosed in U.S. Pat. No. 6,828,567. With this new design approach by eliminating the optical fibers from inside the capillary cartridge, the overall cost of the assembly could be reduced by a factor that could be 10 to 20 times.

Further, the excitation fiber and emission fiber detection configuration in accordance with the present invention provides additional flexibility in the structure of the overall bio-analysis (e.g., CE) instrument, since the radiation source and the detector modules could be part of the complete instrument assembly or could be used as add on modules outside of the instrument. This kind of flexibility gives the end user the option of interchanging the excitation light source (LED, Laser or other broad band light sources) and/or the emission detector (PMT, Si photodiodes or CCD detectors).

* * *

While the invention has been particularly shown and described with reference to the preferred embodiments, it will be understood by those skilled in the art that various changes in form and detail may be made without departing from the spirit, scope, and teaching of the invention.

For example, the excitation radiation source could be, for example, LEDs, Laser Diodes (semiconductor solid-state lasers), pulsed lasers (e.g., solid state lasers, gas lasers, dye lasers, fiber lasers), or other sources of radiation. Alternate relative inexpensive light source for the present invention could be laser diodes in the visible, UV and/or infrared range. For example, laser diodes in the range of 400-900 nm, and more specifically in the range of 400-600 nm may be used, for example.

A person skilled in the art will recognize that the instrument incorporating the essence of this invention can also be used for biomoleculer analysis other than immunoassay and DNA analysis. For example, by altering the separation gel or buffer, the system can also be modified to analyze biomolecules like proteins, carbohydrates, and lipids.

By way of example and not limitation, the detection configuration of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions.

Instead of position the excitation fiber and emission fiber substantially coplanar with the axis of the separation channel at the detection zone, the excitation fiber or the emission fiber may be out of plane, without departing from the scope and spirit of the present invention.

Furthermore, while the separation channels in the described embodiments are defined by cylindrical columns or tubes, it is understood that the concepts of the present invention is equally applicable to separation channels defined by open channels, for example micro-channels defined by etching in a substrate.

Accordingly, the disclosed invention is to be considered merely as illustrative and limited in scope only as specified in the appended claims.

The invention claimed is:

1. A detection system for a bio-separation device in which bio-separation of a sample takes place, comprising:
   a separation channel having a first longitudinal axis along which the sample undergoes separation into sample components, and a detection zone defined along the separation channel through which sample components pass;
   a radiation source;
   a detector;
   an incident light guide having a second longitudinal axis, directing incident radiation from the radiation source to the detection zone, causing radiation to be emitted by sample components as they pass through the detection zone; and
   an emission light guide having a third longitudinal axis, collecting and directing emitted radiation from the detection zone to the detector,
   wherein the emission light guide and the incident light guide are positioned on opposite sides of the separation channel, and wherein the first, second and third longitudinal axis are substantially coplanar at least at or near the detection zone, wherein each of the second and third longitudinal axis makes an acute angle with respect to the first longitudinal axis, wherein at least one of the incident light guide and emission light guide comprises an optical fiber, and wherein the optical fiber has a terminating ball-end structure that is integral to the optical fiber in a unitary structure, and that is spaced apart from exterior of the separation channel.

2. The detection system of claim 1, wherein the radiation source is at least one of LED and laser.

3. The detection system of claim 1, wherein the incident light guide comprises a first optical fiber having a terminating integral ball-end structure, and the emission light guide comprises a second optical fiber having a terminating integral ball-end structure, wherein the ball-end structures do not touch exterior of the separation channel.

4. The detection system of claim 1, wherein the separation channel is defined by a capillary column.

5. The detection system of claim 4, wherein the bio-separation comprises capillary electrophoresis separation.

6. The detection system of claim 1, wherein the emitted radiation is fluorescence radiation, and wherein the incident light causes radiation to be emitted by inducing fluorescence radiation to be emitted by the sample components as they pass through the detection zone.

7. A detection system for a bio-separation device in which bio-separation of a sample takes place, comprising:
   a separation channel having a first longitudinal axis along which the sample undergoes separation into sample components, and a detection zone defined along the separation channel through which sample components pass;
   a radiation source;
   a detector;
   an incident light guide having a second longitudinal axis, directing incident radiation from the radiation source to the detection zone, causing radiation to be emitted by sample components as they pass through the detection zone; and an emission light guide having a third longitudinal axis, collecting and directing emitted radiation from the detection zone to the detector, wherein the emission light guide and the incident light guide are positioned on opposite sides of the separation channel, wherein each of the second and third longitudinal axis makes an acute angle with respect to the first longitudinal axis, and at least one of the incident light guide and emission light guide comprises an optical fiber, and wherein the optical fiber has a terminating ball-end structure that is integral to the optical fiber in a unitary structure.

8. The detection system of claim 7, wherein the incident light guide comprises a first optical fiber having a terminating ball-end structure that is integral to the optical fiber in a unitary structure, and the emission light guide comprises a second optical fiber having a terminating ball-end structure that is integral to the optical fiber in a unitary structure, wherein the ball-end structures do not touch exterior of the separation channel.

9. The detection system of claim 7, wherein the first, second and third longitudinal axis are substantially coplanar at least at or near the detection zone.

10. The detection system of claim 7, wherein the emitted radiation is fluorescence radiation, and wherein the incident light causes radiation to be emitted by inducing fluorescence radiation to be emitted by the sample components as they pass through the detection zone.

11. A cartridge for bio-separation of a sample, comprising:
a body,
a separation channel defined in the body, having a first longitudinal axis along which the sample undergoes separation into sample components, and a detection zone defined along the separation channel through which sample components pass;
an incident light guide having a second longitudinal axis, comprising a first optical fiber having a terminating ball-end structure that is integral to the optical fiber in a unitary structure, directing incident radiation from an external radiation source to the detection zone, causing radiation to be emitted by sample components as they pass through the detection zone; and
an emission light guide having a third longitudinal axis, comprising a second optical fiber having a terminating ball-end structure that is integral to the optical fiber in a unitary structure, collecting and directing emitted radiation from the detection zone to an external detector,
wherein each of the second and third longitudinal axis makes an acute angle with respect to the first longitudinal axis.

12. The cartridge of claim 11, wherein the first optical fiber and the second optical fiber are positioned on opposite sides of the separation channel, and wherein the first, second and third longitudinal axes are substantially coplanar at least at or near the detection zone.

13. The cartridge of claim 12, wherein the separation channel is defined by a capillary column supported on the body.

14. A bio-separation system, comprising:
a cartridge as in claim 11;
a radiation source, wherein the first optical fiber is optically coupled to the radiation source; and
a detector, wherein the second optical fiber is optically coupled to the detector.

15. An electrophoresis system, comprising:
a detection system as in claim 1; and
a power supply providing a voltage across ends of the separation channel to effect electrophoresis separation, wherein separated sample components pass through the detection zone.

16. A method of detecting bio-separation of a sample, comprising:
providing a separation channel having a first longitudinal axis along which the sample undergoes separation into sample components, and defining a detection zone defined along the separation channel through which sample components pass;
providing a radiation source;
providing a detector;
providing an incident light guide having a second longitudinal axis, directing incident radiation from the radiation source to the detection zone, causing radiation to be emitted by sample components as they pass through the detection zone; and
providing an emission light guide having a third longitudinal axis, collecting and directing emitted radiation from the detection zone to the detector,
wherein the emission light guide and the incident light guide are positioned on opposite sides of the separation channel, wherein the first, second and third longitudinal axis are substantially coplanar at least at or near the detection zone, wherein each of the second and third longitudinal axis makes an acute angle with respect to the first longitudinal axis, and wherein the optical fiber has a terminating ball-end structure that is integral to the optical fiber in a unitary structure.

17. The method of claim 16, wherein the emitted radiation is fluorescence radiation, and wherein incident radiation causes radiation to be emitted by inducing fluorescence radiation to be emitted by the sample components as they pass through the detection zone.

* * * * *